United States Patent [19]

Grabenkort

[11] Patent Number: 4,784,658

[45] Date of Patent: Nov. 15, 1988

[54] CONTAINER CONSTRUCTION WITH HELICAL THREADED EXTRACTOR

[75] Inventor: Richard W. Grabenkort, Barrington, Ill.

[73] Assignee: Abbott Laboratories, North Chicago, Ill.

[21] Appl. No.: 9,357

[22] Filed: Jan. 30, 1987

[51] Int. Cl.$^4$ .............................................. A61B 19/00

[52] U.S. Cl. ..................................... 604/410; 604/416

[58] Field of Search ............ 604/82, 89, 91, 408-410, 604/56, 905, 416, 87

[56] References Cited

U.S. PATENT DOCUMENTS

| | | | |
|---|---|---|---|
| 2,969,792 | 1/1961 | Milton . | |
| 3,696,919 | 10/1972 | Miles . | |
| 3,699,961 | 10/1972 | Szpur | 604/89 |
| 4,435,179 | 3/1984 | Walker | 604/410 |
| 4,458,733 | 7/1984 | Lyons | 604/410 |
| 4,589,879 | 5/1986 | Pearson | 604/410 |
| 4,614,267 | 9/1986 | Larkin | 206/221 |
| 4,614,515 | 9/1986 | Tripp et al. | 604/403 |
| 4,657,534 | 4/1987 | Beck et al. | 604/89 |

FOREIGN PATENT DOCUMENTS

| | | | |
|---|---|---|---|
| 0094886 | 1/1970 | France . | |
| 8702239 | 4/1987 | PCT Int'l Appl. | 604/413 |

*Primary Examiner*—C. Fred Rosenbaum
*Assistant Examiner*—Mark O. Polluta
*Attorney, Agent, or Firm*—Neuman, Williams Anderson & Olson

[57] ABSTRACT

A flexible diluent container has a helical threaded port plug which enhances or modifies the mechanical interlock with a stopper of an additive vial in a drug delivery system. The additive vial is screwed into the port of the diluent container with the recess of the vial stopper fitting over the engagement portion of the port plug. In doing so, the helical threads of the port plug engage the stopper throat in a complementary manner to enhance the axial mating engagement therebetween and hence minimize or avoid axial resistance to passage of the large plug head through the neck of the stopper recess. With the helical threads of the port head having a lead greater than the threads of the vial which engage the port, a positive axial drawing action may be obtained so as to induce or "pull" the engagement portion of the port plug into the recess of the stopper. A shoulder at the base of the plug head engages the inward side of the throat shoulder of the stopper, thus providing good gripping on the port plug when the user wants to manipulate the bag and pull the port plug-stopper combination off for the mixing of the contents of the two compartments through the port.

15 Claims, 3 Drawing Sheets

CONTAINER CONSTRUCTION WITH HELICAL THREADED EXTRACTOR

This invention relates to a dual container system having means to effect sterile intermixing of the contents of the two containers by external manipulation after the containers are joined. More particularly, this invention relates to the design of a cover or port plug which enhances or modifies the mechanical interlock between the vial stopper of an additive container and the port plug of a flexible diluent container thus enhancing the reliability of engagement as well as performing satisfactorily with a wide variety of stopper materials of varying resilience and design.

In particular, this invention is for use in systems involving packaging of a medicament and a diluent in separate containers which may be connected to one another at the time of use for convenient safe mixing of the medicament and diluent. Such container systems are known in the art and currently are sold by Abbott Laboratories of North Chicago, Ill. under the trademark ADD-VANTAGE. A number of embodiments of such systems are disclosed in U.S. Pat. Nos. 4,614,267 to Larkin and 4,614,515 to Tripp and Larkin, both of which are assigned to the assignee of this invention. The disclosures in such patents are incorporated herein by reference.

In the noted system the flexible diluent container includes a tubular port which provides a means for securing thereto a stoppered medicament vial as well as a stopper removal means. The stoppers each have a shouldered recess in their exposed end. Previously the stopper removal means was composed of a truncated cone or mushroom shaped engagement element or extractor having a smooth surface and which is attached to a removable cover that covers and seals the inner end of the port. As a stoppered vial is advanced into and engaged with the port, normally by threaded interengagement, the vial stopper advances onto the extractor. The extractor thereby engages the stopper to subsequently pull the stopper from the vial when the cover is pulled from the port.

A wide variety of materials of varying hardness or resilience are used to manufacture vial stoppers since governmental approval is required for the type of material to be used with a particular medicament. Stoppers made from softer materials are more susceptible to being pushed into the medicament vial during engagement by the extractor and/or to the extractor pulling out of the stopper during attempted extraction, whereas stoppers made from harder materials are often more difficult to engage. Difficulty of engagement between the vial stopper and port plug and in insuring the subsequent withdrawal of the stopper also is due in part to the wide variety of physical designs of the vial stoppers e.g., tapered or cylindrical. Of course, the axial insertion force must be less than the force which will remove the port plug from the port closing position.

It is highly desirable to provide a diluent container with a port plug which will provide high reliability of engagement into the stoppers of vials despite variations in materials and designs of those stoppers, to avoid pushing the stoppers into the vials and assuring withdrawal of any stopper with the extractor, and which will avoid pushing the cover off of the inner end of the port.

An important feature of this invention is that the port plug has a universal capability of functioning with vial stoppers made from a wide variety of materials and in a wide variety of designs. It provides very high reliability of engagement between the port plug of the flexible diluent container and vial stopper of the additive medicament vial and of subsequent withdrawal of the stopper.

It is therefore an object and advantage of the present invention to afford a diluent container with a port plug which has the aforementioned and other capabilities.

SUMMARY OF THE INVENTION

This invention relates to diluent containers with a new design of a port plug such as to enhance or facilitate the intermating between the vial stopper of the additive container and the vial port plug of the flexible diluent container thus providing high or absolute reliability of engagement. This is accomplished by a helically threaded plug design which mitigates the axial force transfer from the port plug to the stopper during interengagement while preserving or increasing the size of the engagement head and thus the amount of force which can be transmitted therebetween subsequently for removing the stopper. In this manner the port fluid seal and vial stopper seal are maintained while the additive vial is engaged into the port of the flexible diluent container and the vial stopper becomes reliably engaged to the port plug of the flexible diluent container This, in turn, enables the user to manipulate the bag and pull the stopper from the attached vial by pulling the port plug inwardly off the port, thus resulting in the mixing of the contents of the two compartments through the port. Normally this involves dumping of the contents of the vial into the diluent in the bag.

In the particular design of this invention the medicament vial typically is screwed into the port of the diluent container with the recess of the vial stopper fitting over the engagement portion of the port plug. In doing so, the helical threads of the port plug engage the stopper throat in a complementary manner to enhance the axial mating engagement therebetween and hence minimize or avoid axial resistance to passage of the large plug head through the neck of the stopper recess. With the helical threads of the port head having a lead greater than the threads of the vial which engage the port, a positive axial drawing action may be obtained so as to induce or "pull" the engagement portion of the port plug into the recess of the stopper. Once the port plug is fully seated, the shoulder at the base of the plug head engages the inward side of the throat shoulder of the stopper thus providing good gripping on the port plug when the user wants to manipulate the bag and pull the port plug-stopper combination. The projecting threads also may remain in engagement with the surrounding wall portions of the stopper or contribute to the engagement on the throat shoulder.

DESCRIPTION OF THE DRAWINGS

A better understanding of the invention will be had by reference to the embodiment illustrated in the drawings wherein.

DESCRIPTION OF PREFERRED EMBODIMENT

Figure 1:
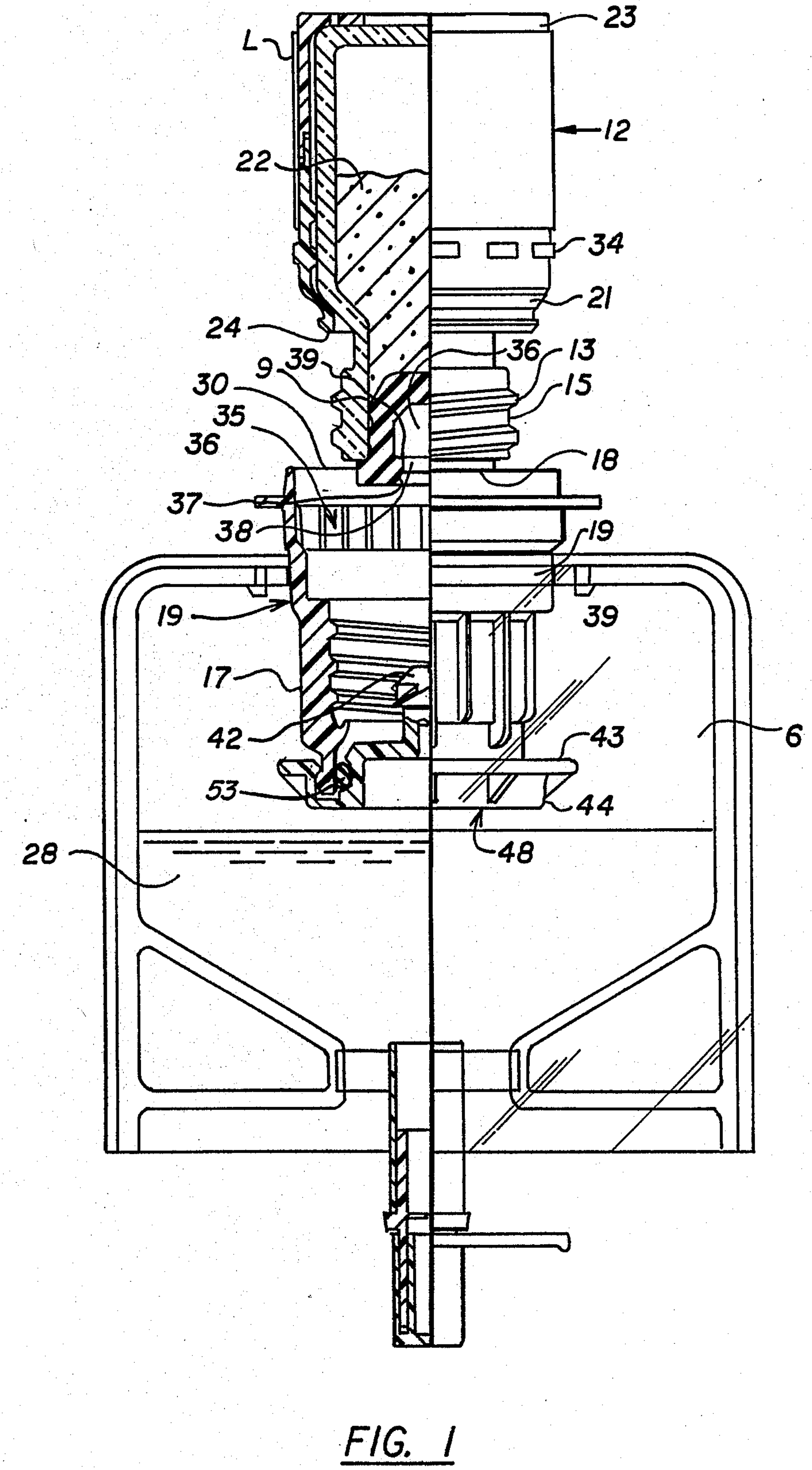
FIG. 1 is a front view, partially in section, of a flexible diluent container employing teachings of this invention and an aligned additive medicament vial before being secured to the flexible diluent container.

Proceeding to a detailed description of the illustrated embodiment of the invention, FIG. 1 illustrates an additive medicament vial 12 just prior to being secured to the flexible diluent container 6. The diluent container typically is supplied with a protective cap over the outer end of the port, see for example the closure disclosed in the copending application of Larkin, Tripp and Ziegler, Ser. No. 806,782, filed Dec. 9, 1985 and assigned to the assignee of this invention, the disclosure of which is incorporated herein by this reference. Such a closure is not shown in FIG. 1, it being assumed that the port has been opened by the health care technician in preparation for engagement of the vial. As previously indicated, the additive medicament vial will be supplied independently of the flexible container with the interconnection being effected, for example, by the health care technician. Typically the medicament vial is supplied with a stopper 18 in the vial opening 9 and a removable cap covering the stopper for maintaining sterility as described in U.S. Pat. No. 4,614,515. The cap is attached to a skirt member 21 which is circumscribed by a ring of ratchet teeth 34. A 25 shroud 23 covers the lower portion of the vial. A label L overlaps the skirt and the shroud. The neck and discharge end portion 15 of the vial is exposed for engagement with the diluent container by tearing off the cap along an annular tear line at 24, as described in said U.S. Pat. No. 4,614,515. Once the cap is removed from the vial and from the outer end of the port, the vial may be inserted into the port 30 of the flexible container 6 with the ring of ratchet teeth 34 engaging complementary teeth 35 on the port to prevent easy removal of the vial.

Vial 12 has the usual end portion 15 with threads 13 extending therefrom. Complementary threads 17 extend internally from port 30 which is mandrel sealed at 19 to the walls of the flexible container 6. The stopper 18 is formed with a recess 36 with an annular lip or flange 37 defining an entrance throat 38 of reduced diameter and an annular internal shoulder 39 on its back or inward side.

When it is desired to mix the contents 22 of a vial 12 into a solution container 6, the caps are removed from the vial and from the outer end of the port, and the vial and solution container components are brought into mating alignment as in FIG. 1. Then the vial 12 is screwed into port 30 resulting in the recess 36 of vial stopper 18 fitting over the engagement portion 42 of the port plug 48. The contents of vial 12 and the contents 28 of the flexible container 6 may then be mixed by dumping the contents of vial 12 into the container 6, by removing the port plug-engaged stopper combination. This is accomplished by manually pulling on the rim 43 of the cover portion 44 of the plug by manipulation from the exterior of the flexible bag 6, i.e., through the flexible container walls, as described further in the aforementioned patents.

Figure 2:
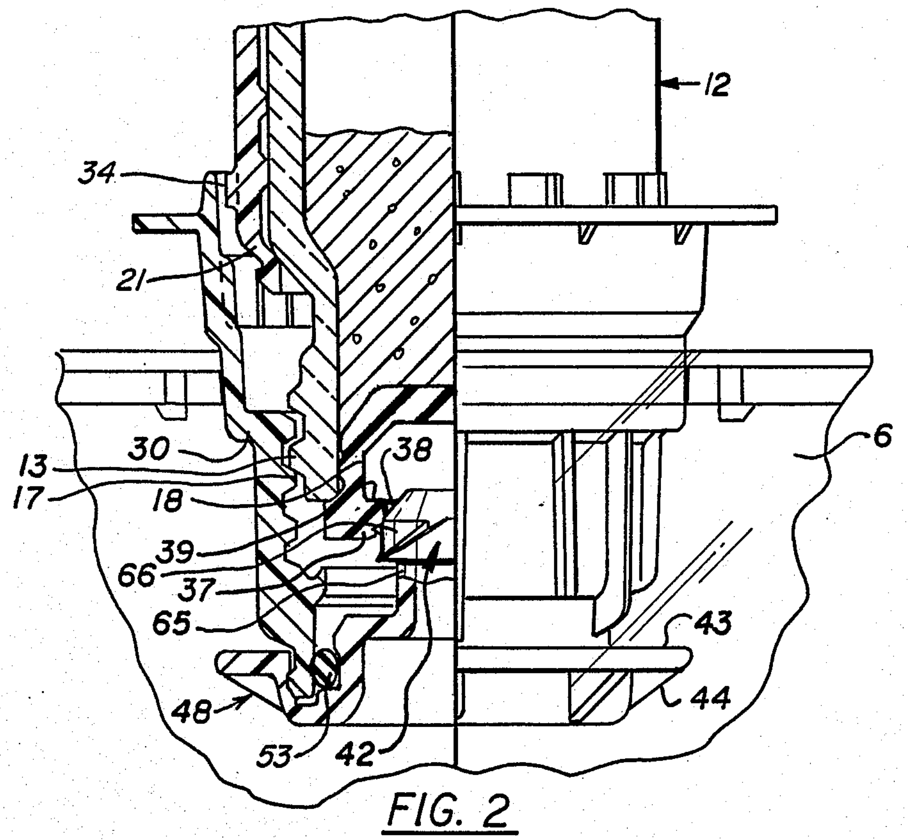
FIG. 2 is an enlarged partial view similar to FIG. 1 as the vial is being engaged with the flexible container.

FIG. 2 is an enlarged partial view of the engagement of the vial stopper of the additive container and the port plug of the flexible diluent container as the vial is being inserted into the port 30. The stopper 18 of the vial 12 is mated onto the engagement portion 42 of the port plug 48 as the vial is rotated and advanced in effecting the threaded engagement of the vial neck in the port at 13, 17. Helical threads 65 are provided on the plug head 66 (see also FIG. 5) to engage the stopper flange 37 in throat 38 as the vial and its stopper are rotated, thereby to induce the axial engagement of the large plug head into and through the smaller opening of the stopper recess. This reduces or avoids the axial forces that would otherwise be transmitted to the stopper when thrusting the plug head 66 through the throat 38 of the stopper. Preferably this inducement to mating engagement between the plug head and the stopper is accomplished by the lead of the threads 65 being greater than the lead of the threads 13 and 17 of the vial and the port 30. This lead relationship tends to cause greater relative axial motion between the vial and the stopper than is occurring by virtue of the threading of the vial into the port, thus tending to result in a drawing action between the port plug 48 and the stopper 18.

Figure 3:
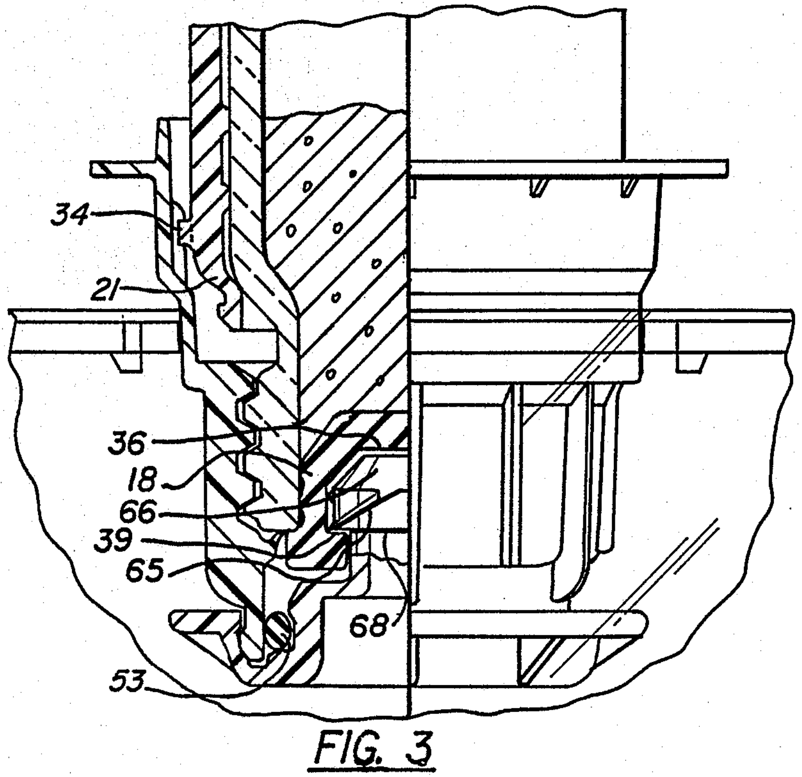
FIG. 3 is a view similar to FIG. 2 showing the vial fully engaged, with the port plug of the flexible container seated in the recess of the stopper

The stopper is rotated onto the head 66 as the vial is rotated into the threads 17 by virtue of the frictional engagement of the stopper in the vial neck. This insertion step is illustrated in FIG. 2 where the leading edge of stopper 18 is inserted approximately halfway into port 30. Once the vial stopper is fully seated, as is shown in FIG. 3, the plug head 66 has fully entered recess 36. The proximal shoulder 68 on the head is disposed inward of the flange 37 and thus provides good interference gripping on the lateral shoulder 39 of the stopper when the user wants to manipulate the bag and pull the port plug-stopper combination from the seated, sealing position of FIG. 3. The threads 65 further increase the effective width of the shoulder 68, and may continue to be in an engaging gripping relationship with the peripheral wall of the recess 36.

Figure 4:
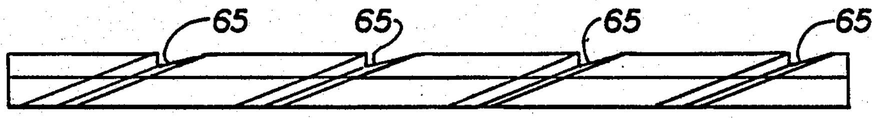
FIG. 4 is an enlarged developmental view of the four lead threads which form the engagement portion of the port plug of the diluent container of FIG. 1.

FIG. 4 depicts a developed view of the lead threads 65 on the engagement head portion 66 of the port plug 48. In the illustrated embodiment, there are four helical lead threads 65 uniformly spaced about the periphery of the head 66. The helical lead threads 65 for a lead angle 88, i.e. the angle of the threads 65 in relation to a plane normal to the axis of the head portion 66.

Figure 5:
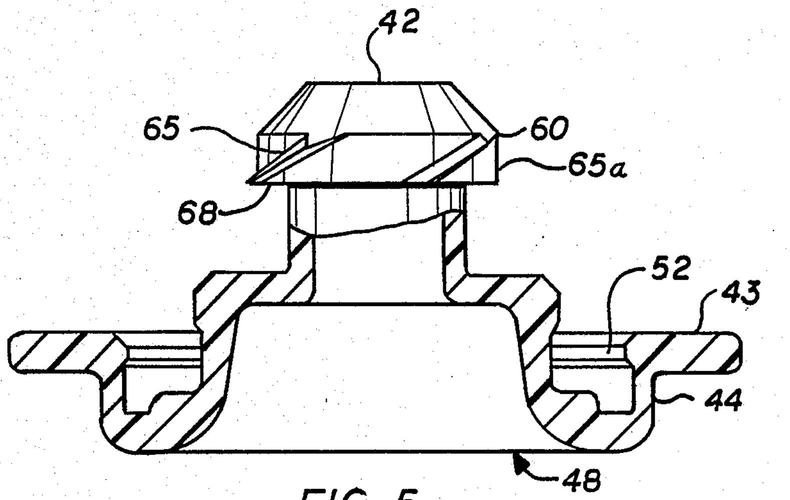
FIG. 5 is a side view, partially in center section, of the port plug of the embodiment of FIG. 1.

FIG. 5 depicts a partially sectional view of the vial port plug. An annular recess 52 is provided in port plug 48 to receive the inner annular end of the port 30 and an O-ring seal 53 as seen in FIGS. 1, 2 and 3. A lip at the inner edge of rim 43 effects retentive latching engagement with a similar lip on the port; see FIGS. 2 and 3. The engagement or extractor portion 42 of the port plug 48 is tapered from a minimum diameter smaller than the diameter of throat 38 to the outer periphery of the head 66 to facilitate and ease movement of the head and threads 65 into and through the resilient throat by pressing outward the engaged portion of lip 37. This enables engagement portion 42 to easily enter recess 36 of vial stopper 18 and facilitates engagement of the threads 65 in the throat 38. As noted above, the helical threads 65 then act to facilitate and induce the movement of the head 66 into the recess 36 as the vial is rotated and threaded into its seated position. The lead of threads 65 should be approximately equal to or greater than the lead of threads 13, 17 to avoid pushing the stopper away from the engaging head 66 into the vial, and preferably is substantially greater to gain a relative drawing action between the head 66 and the engaged portion of the stopper as noted above. Such threading engagement is particularly advantageous when the stopper 18 is composed of relatively firm, less resilient materials. The outer diameter dimension across the proximal edges of the helical threads 65 is approximately equal to the diameter of the recess 36 inward of the lip 37, see FIG. 3.

Figure 6:
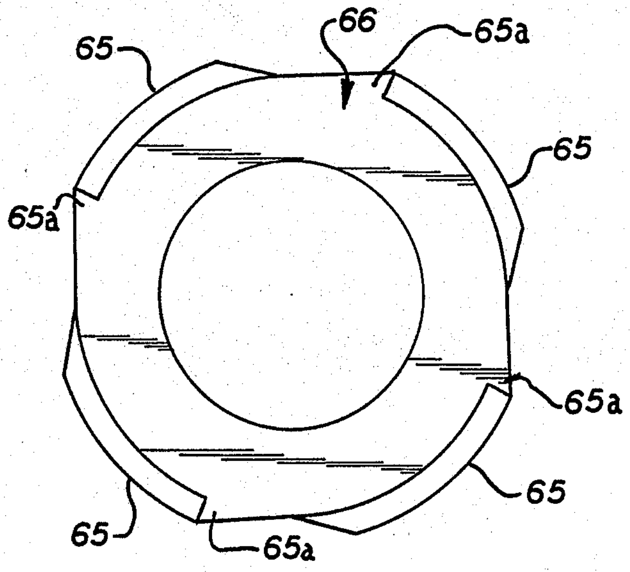
FIG. 6 is a top view of the extractor portion of the port plug of FIG. 5, with four helical threads.
Figure 7:
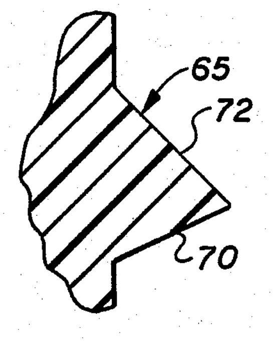
FIG. 7 is an enlarged fragmentary sectional view through one of the helical threads of FIG. 4.

FIG. 6 further illustrates the disposition of the helical threads 65 and the taper affected at their leading ends 65*a* to facilitate entry into the throat 38. The outer edges are sharp, as best seen in FIG. 7. A number of parameters can be varied in regards to the design of the port plug including the number of helical threads, their pitch diameter and lead, and thus helical lead angle, and the diameter of the head 66 of the port plug itself.

A specific illustrative embodiment of the port plug is the four lead thread version as illustrated in FIGS. 4–7. Here the thread pitch is 0.112" and the lead is 0.448". The outside diameter of the main body of the head 66 and the minor diameter of the helical threads 65 is 0.362" and the major (outside) diameter of the helical threads 65 is 0.402". The height of each helical thread 65 thus is about 0.020" and the lead angle is about 21°. Each thread is very sharp, with a proximal face 70 about 23° and a distal face 72 about 45° to a plane normal to the helical axis. Each of the four helical threads 65 extends over about 0.248" of the circumference of head 66 and is spaced about 0.036" from adjacent threads when measured in the flat as in FIG. 4. Such a head was used for engaging stoppers having a throat about 0.282" in diameter, a recess about 0.362" in diameter and a lip flange about 0.100" thick in a vial having two lead threads 13 having a pitch of 0.125", pitch diameter of about 0.81", a lead of 0.250" and a lead angle 88 of about 5.6°.

OPERATION

After the closure is removed from a diluent container 6 and the end cap is removed from a selected vial 12, the vial is ready to be inserted into the flexible container 6 as shown in FIG. 1. In this position the medicament vial 12 is ready to be screwed into the port 30. The interengagement of vial 12 and port 30 is accomplished by threadable engagement of threads 13 with complementary threads 17 within port 30. Rotating vial 12 with respect to the flexible container 6 causes end 15 to be drawn into port 30. This drawing action causes engagement portion 42 of the port plug 48 to enter the recess 36 in stopper 18 as well as effecting sealing engagement of the vial with the port. As the vial 12 is screwed into port 30 and stopper 18 is rotated by the vial, the threads 65 on the port plug threadably engage the stopper to induce engagement of the stopper onto the extractor and reduce the amount of axial insertion force otherwise imparted to the stopper. When engagement portion 42 has completely entered recess 36, the threads and shoulder fully and positively engage the stopper. The ratchet teeth 34 engage the compatible ratchet teeth 35 in the port, thus preventing the vial 12 from being easily backed out of port 30 once interengagement has begun. With the port plug 48 fully seated as is shown in FIG. 3 a great amount of force is required to disengage the port plug from the stopper 18. This ensures that the stopper 18 will be removed from the vial 12 when the port plug is removed from the port 30 by manually manipulating the cover 44 from the exterior of the flexible container 6 without the stopper and port plug becoming disengaged from one another Such removal of the port plug 48 and stopper 18 combination will create an open path through vial opening 9 for medicament 22 to intermix with diluent 28. Diluent 28 and medicament 22 may be further intermixed by squeezing the sides of the flexible container 6. The preferred material for the port plug is a polypropylene copolymer.

The invention has been described as used in one particular system. Activation of the drug delivery system including the mixing of the medicament and diluent by removal of the port plug-stopper combination may be readily accomplished by health care or pharmacy personnel without the use of specially designed components or sophisticated methods which require an excessive number of procedures or prolonged exposure which might jeopardize sterility. It will be appreciated that the invention may be embodied in other similar systems.

The foregoing invention can now be practiced by those skilled in the art. Such skilled persons will know that the invention is not necessarily restricted to the particular embodiments presented herein. The scope of the invention is to be defined by the terms of the following claims as given meaning by the preceding description

What is claimed is:

1. A flexible diluent container including an access port having first means for engaging the outlet portion of a second container which is closed by a removable resilient stopper having a recess in an exposed end of such stopper, said flexible container including extractor means comprising an engagement portion protruding along a first axis for engaging such a stopper within said recess thereof, for removal of the stopper from such a second container when engaged with said first means, wherein said engagement portion comprises helical thread means exposed on the periphery of said engagement portion and of a diametral dimension substantially greater than the diametral dimension of at least a portion of said recess for engagement of said helical thread means into the resilient material of such a stopper around the periphery of at least said portion of such recess therein, to facilitate entry of said engagement portion into the recess for thereafter engaging the stopper for effecting removal of said stopper by said extractor means.

2. The invention as defined in claim 1 wherein said extractor means is affixed to a cover which closes the inner end of said port and extends from said cover into said port.

3. The invention as in claim 1 in which said first means includes means in said port for engagement of such an outlet portion of a second container by rotation of such second container relative to said port and said helical threads are oriented to threadably advance into such stopper upon such relative rotation of such second container.

4. The invention as in claim 3 wherein said helical thread means has a lead angle greater than the lead angle of said means for engaging such an outlet portion of a second container in said port.

5. The invention as in claim 3 wherein said outlet portion of said second container and said port include complementary threadable engagement elements.

6. The invention as in claim 5 wherein said helical thread means has a lead angle greater than the lead angle of said complementary engagement elements.

7. The invention as defined in claim 1 wherein said engagement portion comprises a plug head and said helical thread means includes a plurality of spaced thread segments protruding from the periphery of said plug head.

8. The invention as defined in claim 7 wherein said plug head includes a proximal shoulder for engaging an internal shoulder of such a stopper within the recess therein.

9. The combination of a vial which has a removable resilient stopper with a recess in an exposed end thereof, and a port plug comprising extractor means including an engagement portion protruding along a first axis for engaging said stopper within said recess for removal of said stopper from said vial, wherein said engagement portion of said port plug comprises helical thread means exposed on the periphery of said engagement portion and of a diametrical dimension substantially greater than the diametral dimension of at least a portion of said recess for engagement of said helical thread means into the resilient material of said stopper around the periphery of at least said portion of said recess to facilitate entry of said engagement portion into said recess for thereafter engaging the stopper for effecting removal of said stopper by said extractor means.

10. The invention as defined in claim 9 wherein said extractor means is affixed to a cover for closing a port opening spaced from said vial.

11. The invention as defined in claim 9 wherein said recess includes a throat portion and an inner portion of larger cross-section than said throat portion and defining a shoulder on the inward side of said throat portion, said engagement portion being of a larger cross-section than said throat portion and including a proximal shoulder for engaging said internal shoulder when said engagement portion is seated in said recess.

12. The invention as in claim 9 wherein said engagement portion includes a plug head of larger cross-section than said recess and said thread means includes a plurality of spaced thread segments protruding from the periphery of said plug head.

13. A port plug comprising a port cover and extractor means including an engagement portion extending from said cover along a first axis for engaging a resilient stopper within a recess in the exposed end of the stopper for removal of such stopper from a vial, wherein said engagement portion of said port plug comprises a plurality of helical threads extending generally radially from said first axis and of a diametrical dimension substantially greater than the diametral dimension of at least a portion of said recess for engagement of said helical threads into the resilient material of such a stopper around the periphery of at least said portion of such a recess to facilitate entry of said engagement portion into the recess of such a stopper for effecting removal of said stopper by said extractor means.

14. The invention of claim 13 for engaging a stopper which defines an entrance throat of said recess and an internal annular shoulder located inward of such recess relative to said throat, said extractor including a plug head having a proximal shoulder for engaging said annular shoulder when said plug head is seated in said inner recess, and said helical threads comprise helical thread segments protruding from the periphery of said plug head to facilitate passage of said plug head through such throat into said recess.

15. The invention as in claim 14 wherein the outside diametral dimension defined by the edges of said helical thread segments substantially exceeds the lateral dimension of said recess outward for said shoulder.

* * * * *